US010175222B2

(12) United States Patent
Kim et al.

(10) Patent No.: US 10,175,222 B2
(45) Date of Patent: Jan. 8, 2019

(54) NANOPORE STRUCTURE, IONIC DEVICE USING NANOPORE STRUCTURE AND METHOD OF MANUFACTURING NANOMEMBRANE STRUCTURE

(71) Applicant: Seoul National University R&DB Foundation, Seoul (KR)

(72) Inventors: Ki-Bum Kim, Seoul (KR); Jae-Seok Yu, Seoul (KR); Hyung-Jun Kim, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 305 days.

(21) Appl. No.: 14/901,119

(22) PCT Filed: Jul. 16, 2015

(86) PCT No.: PCT/KR2015/007399
§ 371 (c)(1),
(2) Date: Dec. 28, 2015

(87) PCT Pub. No.: WO2017/003006
PCT Pub. Date: Jan. 5, 2017

(65) Prior Publication Data
US 2017/0138925 A1    May 18, 2017

(30) Foreign Application Priority Data
Jul. 1, 2015   (KR) .................. 10-2015-0094159

(51) Int. Cl.
*H01L 21/00* (2006.01)
*B32B 3/26* (2006.01)
(Continued)

(52) U.S. Cl.
CPC ... *G01N 33/48721* (2013.01); *B81C 1/00087* (2013.01); *H01L 21/465* (2013.01);
(Continued)

(58) Field of Classification Search
CPC ............ B01D 67/0062; B01D 2325/24; B82Y 15/00; B82Y 40/00; H01L 21/465
See application file for complete search history.

(56) References Cited

U.S. PATENT DOCUMENTS 7,655,075 B2 *  2/2010  Hofmann ........... B01D 67/0062
                                               210/490
7,662,218 B2 *  2/2010  Maeda ................. B01D 53/228
                                               205/265
(Continued)

FOREIGN PATENT DOCUMENTS

| KR | 1020120065792 A | 6/2012 |
| KR | 1020130019699 A | 2/2013 |
| KR | 1020130143429 A | 12/2013 |

OTHER PUBLICATIONS

International Search Report dated Mar. 29, 2016 for corresponding foreign Application No. PCT/KR2015/007399, 3 pp.
(Continued)

*Primary Examiner* — Joseph C Nicely
*Assistant Examiner* — David Goodwin
(74) *Attorney, Agent, or Firm* — United IP Counselors, LLC (57) ABSTRACT

A method of manufacturing a nano membrane structure includes preparing a temporary structure having a substrate in which a through-hole is formed in a central portion, and a nano membrane including silicon nitride (SiN), that covers the through-hole on the substrate, and including a central area formed on the through-hole, and a peripheral area formed on the substrate. The method includes preparing an insulating support member including at least one of silicon and a compound containing silicon, and in which a micropore is formed in a central portion, forming a complex structure by performing a hydrophilic surface processing of a surface of the nano membrane and one surface of the insulating support member and by bonding the temporary structure and the insulating support member so that at least a portion of the central area of the nano membrane and the micropore face, and removing the substrate from the complex structure.

10 Claims, 12 Drawing Sheets

(51) Int. Cl.
*G01N 27/414* (2006.01)
*G01N 33/487* (2006.01)
*H01L 21/465* (2006.01)
*H01L 29/24* (2006.01)
*B81C 1/00* (2006.01)
*C12Q 1/6869* (2018.01)

(52) U.S. Cl.
CPC ...... *H01L 29/24* (2013.01); *B81B 2201/0214* (2013.01); *B81B 2203/0127* (2013.01); *B81B 2203/0353* (2013.01); *C12Q 1/6869* (2013.01)

(56) References Cited

U.S. PATENT DOCUMENTS

| | | | | |
|---|---|---|---|---|
| 8,182,590 B2* | 5/2012 | Striemer | ................ | B01D 61/18 210/500.21 |
| 8,361,196 B2* | 1/2013 | Schwartz | .............. | G01M 3/205 204/415 |
| 9,085,120 B2* | 7/2015 | Astier | ................ | G01N 27/4145 |
| 2005/0018017 A1* | 1/2005 | Silverbrook | ............... | B41J 2/14 347/54 |
| 2005/0092676 A1* | 5/2005 | Dalton | ................ | B01D 67/0034 210/500.26 |
| 2006/0068401 A1 | 3/2006 | Flory et al. | | |
| 2007/0023850 A1* | 2/2007 | Chen | .................... | H01L 21/187 257/414 |
| 2010/0300882 A1* | 12/2010 | Zhang | .................. | B01D 63/087 204/543 |
| 2012/0182548 A1* | 7/2012 | Harb | ...................... | G01N 21/05 356/246 |
| 2016/0282326 A1* | 9/2016 | Waduge | ............... | C23C 16/0281 |
| 2017/0307587 A1* | 10/2017 | Yanagi | ............. | G01N 33/48721 |

OTHER PUBLICATIONS

Office Action dated Jan. 6, 2017 for Korean Application No. 10-2015-0094159, 5 pp.

* cited by examiner

NANOPORE STRUCTURE, IONIC DEVICE USING NANOPORE STRUCTURE AND METHOD OF MANUFACTURING NANOMEMBRANE STRUCTURE

CROSS-REFERENCES TO RELATED APPLICATIONS

This application is the U.S. National Phase of PCT International Application No. PCT/KR2015/007399, filed on Jul. 16, 2015. That application claims priority to Korean Patent Application No. 10-2015-0094159, filed Jul. 1, 2015. The contents of both applications are herein incorporated by reference in their entirety.

BACKGROUND

Technical Field

The present invention relates to a nanopore structure, an ion device using a nanopore structure, and a method of manufacturing a nano membrane structure, and more particularly, to a nanopore structure body using a nanopore structure formed on an insulating support member, an ion device using a nanopore structure, and a method of manufacturing a nano membrane structure.

Description of the Related Art

A nanopore was started as DNA base sequence analysis technology using α-hemolysin, which is protein of a form structurally having a hole of a nano size. After putting a protein nanopore in an electrolyte containing DNA, when applying a voltage to electrodes of both sides, DNA having negative electric charges passes through a nanopore of 1.5 nm. In this case, when measuring a current drop occurring while DNA blocks a flow of ions, it can be seen that which base sequence has passed through and thus a DNA base sequence may be analyzed. However, in a protein nanopore, a size thereof is structurally fixed to 1.5 nm and the protein nanopore has no good stability and thus the protein nanopore has a fatal drawback that measurement is available only for a short time of less than 1 hour.

In order to overcome such limitations, a solid-state nanopore having free fore size controllability and excellent stability was appeared. A method of stably forming a silicon nitride (SiN) nanopore through a semiconductor process based on silicon (Si) has been developed to be used as an instrument for analyzing various biomolecules or nano particles such as protein, RNA, and virus in addition to DNA base sequence analysis. However, because an ion device using a silicon nitride nanopore formed on a silicon substrate has no good signal to noise ratio, the ion device has a limitation in various use and accurate analysis.

In order to solve a noise problem of such an ion device using a nanopore based on silicon, various attempts have been suggested. A method of reducing an exposure area on an electrolyte of a silicon nitride nanopore membrane, a method of coating or depositing a dielectric material such as silicon oxide (SiO2) or polydimethylsiloxane (PDMS) in an upper portion or a lower portion of a silicon nitride nanopore membrane, and a method of using an insulating support member such as polydimethylsiloxane (PDMS) or glass instead of silicon are representative methods. When using such a method, while adjusting a size of a nanopore and a thickness of a nanopore membrane to a nanometer level, a signal to noise ratio may be remarkably enhanced.

However, in an ion device in which a silicon nitride nanopore membrane is formed on an insulating support member, there is a drawback that it is not easy to transfer the silicon nitride nanopore membrane onto the insulating support member. Particularly, polymethyl methacrylate (PMMA) used as a transfer support layer of a silicon nitride nanopore membrane is not completely removed but remained as a residual material even after transfer of the silicon nitride nanopore membrane to deteriorate accuracy of analysis.

BRIEF SUMMARY

The present invention has been made in an effort to provide a method of easily forming a nano membrane on an insulating support member, a nanopore structure, and an ion device using the nanopore structure.

An exemplary embodiment of the present invention provides a nanopore structure including: an insulating support member including at least one of silicon and a compound containing silicon and in which a micropore that penetrates one side and the other side is formed in a central portion; and a nanopore film including silicon nitride (SiN), disposed on the insulating support member, and in which a nanopore having a size smaller than that of the micropore is formed in a central portion in order to communicate with the micropore, wherein the nanopore film and the insulating support member are attached by a hydrophilic surface processing.

The nanopore film and the insulating support member may be attached under water.

The insulating support member may include at least one of silicon (Si), silicon oxide (SiO2), silicon nitride (SiN), and polydimethylsiloxane (PDMS).

The insulating support member may include a silicon oxide substrate and an amorphous silicon layer formed on the silicon oxide substrate, and the nanopore film and the amorphous silicon layer may be attached.

The nanopore film may include silicon nitride formed by Low Pressure Chemical Vapor Deposition (LPCVD).

Another embodiment of the present invention provides an ion device using a nanopore including: a chamber including a first area and a second area; a first electrode located at the first area; a second electrode located at the second area to be opposite to the first electrode; an insulating support member located between the first electrode and the second electrode, including at least one of silicon and a compound containing silicon, and in which a micropore that penetrate one side and the other side is formed in a central portion; and a nanopore film including silicon nitride (SiN), disposed on the insulating support member, and in which a nanopore having a size smaller than that of the micropore is formed in a central portion in order to communicate with the micropore, wherein the nanopore film and the insulating support member are attached by a hydrophilic surface processing, and an ion movement passing through the nanopore occurs by an electrical signal applied to the first electrode and the second electrode.

The nanopore film and the insulating support member may be attached under water.

The insulating support member may include at least one of silicon (Si), silicon oxide (SiO2), silicon nitride (SiN), and polydimethylsiloxane (PDMS).

The insulating support member may include a silicon oxide substrate and an amorphous silicon layer formed on the silicon oxide substrate, and the nanopore film and the amorphous silicon layer may be attached.

The nanopore film may include silicon nitride formed by Low Pressure Chemical Vapor Deposition (LPCVD).

In the chamber, an electrolyte solution may be housed, and the ion movement may occur by an electrolyte included in the electrolyte solution.

An ion movement passing through the nanopore may occur or may be blocked by an electrical signal applied to the nanopore film, the first electrode, and the second electrode.

Yet another embodiment of the present invention provides a method of manufacturing a nano membrane structure, the method including: preparing a temporary structure having a substrate in which a through-hole is formed in a central portion and a nano membrane including silicon nitride (SiN) and that covers the through-hole on the substrate and including a central area formed on the through-hole and a peripheral area formed on the substrate; preparing an insulating support member including at least one of silicon and a compound containing silicon and in which a micropore is formed in a central portion; forming a complex structure by performing a hydrophilic surface processing of a surface of the nano membrane and one surface of the insulating support member and by bonding the temporary structure and the insulating support member so that at least a portion of a central area of the nano membrane and the micropore face; and removing a substrate from the complex structure.

The forming of a complex structure may be performed under water.

The method may further include drying the complex structure between the forming of a complex structure and the removing of a substrate.

The method may further include forming a nanopore communicating with the micropore and having a size smaller than that of the micropore in a central area of the nano membrane.

The removing of a substrate may include physically removing the substrate.

The removing of a substrate may include together removing a peripheral area of the nano membrane, when removing the substrate.

The insulating support member may include at least one of silicon (Si), silicon oxide (SiO2), silicon nitride (SiN), and polydimethylsiloxane (PDMS).

The insulating support member may include a silicon oxide substrate and an amorphous silicon layer formed on the silicon oxide substrate, and the forming of a complex structure may include forming a complex structure by bonding the nano membrane and the amorphous silicon layer.

The nano membrane may include silicon nitride formed by Low Pressure Chemical Vapor Deposition (LPCVD).

The drying of the complex structure may be performed in a temperature of 100° or less.

The method may further include etching the nano membrane between the drying of the complex structure and the forming of a nanopore.

The forming of a nanopore may include forming a hole of a nano size using an E-beam.

The substrate may be a silicon substrate, and a central area of the nano membrane may have a square shape having a size of several mm and have a size larger than that of the micropore.

According to the present invention, an insulating support member and a nano membrane can be easily attached by a hydrophilic surface processing and dry. A nanopore structure having a clean surface can be formed with such a simple method.

BRIEF DESCRIPTION OF THE DRAWINGS

The objects, features and advantages of the present invention will be more apparent from the following detailed description in conjunction with the accompanying drawings, in which.

DETAILED DESCRIPTION OF EXEMPLARY EMBODIMENTS

Hereinafter, exemplary embodiments of the present invention are described in detail with reference to the accompanying drawings.

Exemplary embodiments of the present invention are provided to further completely describe the present invention to a person of ordinary skill in the art, and the following exemplary embodiments may be changed to several different forms, and the scope of the present invention is not limited to the following exemplary embodiments. These exemplary embodiments enable to further complete the present disclosure and are provided to completely transfer the spirit of the present invention to a person of ordinary skill in the art.

In the drawings, a shown shape may be changed according to, for example, production technology and/or tolerance. Therefore, an exemplary embodiment of the present invention is not limited to a specific shape of an area shown in this specification but should include, for example, a shape change that may occur when producing. Like reference numerals designate like elements throughout the specification. Further, various elements and areas in the drawings are schematically shown. Therefore, the present invention is not limited to a relative size or gap shown in the accompanying drawings.

Figure 1:
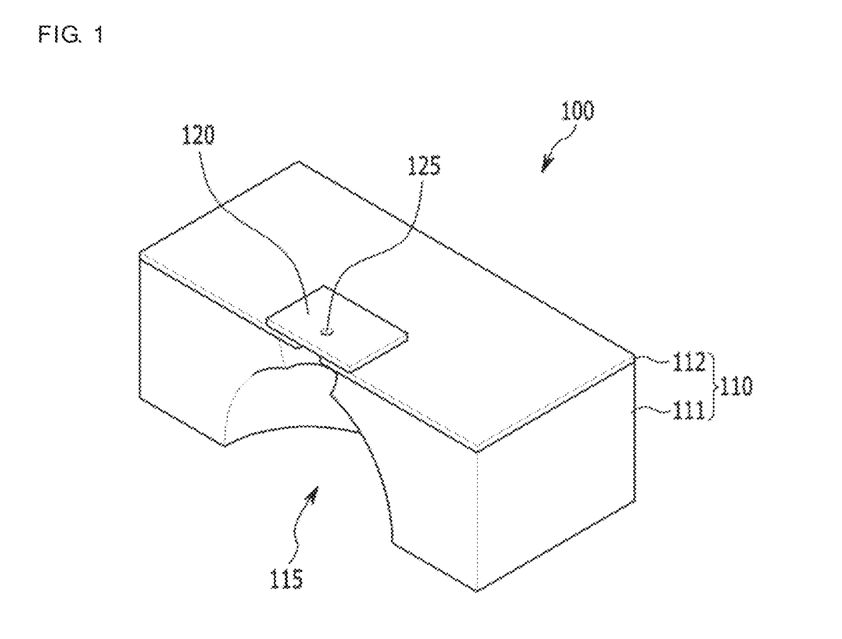
FIG. 1 is a perspective view illustrating a nanopore structure according to an exemplary embodiment of the present invention.

FIG. 1 is a perspective view illustrating a nanopore structure according to an exemplary embodiment of the present invention.

Referring to FIG. 1, a nanopore structure 100 according to the present exemplary embodiment includes an insulating support member 110 and a nanopore film 120.

The insulating support member 110 may be made of an insulating material including at least one of silicon and a compound containing silicon. The insulating support member 110 may include at least one of, for example, silicon (Si), silicon oxide (SiO2), silicon nitride (SiN), and polydimethylsiloxane (PDMS). The insulating support member 110 may be formed with a silicon oxide substrate 111 and an amorphous silicon layer 112 formed on the silicon oxide substrate 111.

In a central portion of the insulating support member 110, a micropore 115 that penetrates one side and the other side is formed. The micropore 115 may be formed in a size of several micrometers. The micropore 115 may be formed using an etching process. Here, a size of the micropore 115 is defined to a size of a hole formed at an upper surface of the insulating support member 110, i.e., the nanopore film 120 and a corresponding surface, and as advancing to a lower portion of the insulating support member 110, a size of the micropore 115 may increase. For example, when the insulating support member 110 is formed with the silicon oxide substrate 111 and the amorphous silicon layer 112 formed on the silicon oxide substrate 111, a size of the micropore 115 is defined to a size of a hole formed in the amorphous silicon layer 112, a size thereof may be several micrometers, and a size of a hole formed in the silicon oxide substrate 111 may be tens to hundreds of micrometers.

The nanopore film 120 is disposed on the insulating support member 110. The nanopore film 120 may include silicon nitride (SiN), and in a central portion of the nanopore film 120, a nanopore 125 is formed. The nanopore 125 is formed to communicate with the micropore 115 of the insulating support member 110 and is formed in a size smaller than that of the micropore 115. The nanopore 125 may be formed in a nano size and may be formed using an E-beam. The nanopore film 120 may have a thickness from several nanometers to tens of nanometers.

The nanopore film 120 may be silicon nitride formed by a Low Pressure Chemical Vapor Deposition (LPCVD) method. Silicon nitride formed by the LPCVD method has a higher density than that of silicon nitride formed by a Plasma Enhanced Chemical Vapor Deposition (PECVD) method and may thus be used for a long time without a size change of the nanopore 125.

As the insulating support member 110 and the nanopore film 120 are attached by a hydrophilic surface processing, the nanopore structure 100 is formed. By supplying moisture to a surface of each of the insulating support member 110 and the nanopore film 120 and by bonding and drying the insulating support member 110 and the nanopore film 120, the nanopore structure 100 may be formed. For this reason, the insulating support member 110 and the nanopore film 120 may be attached under water.

Figure 2A:
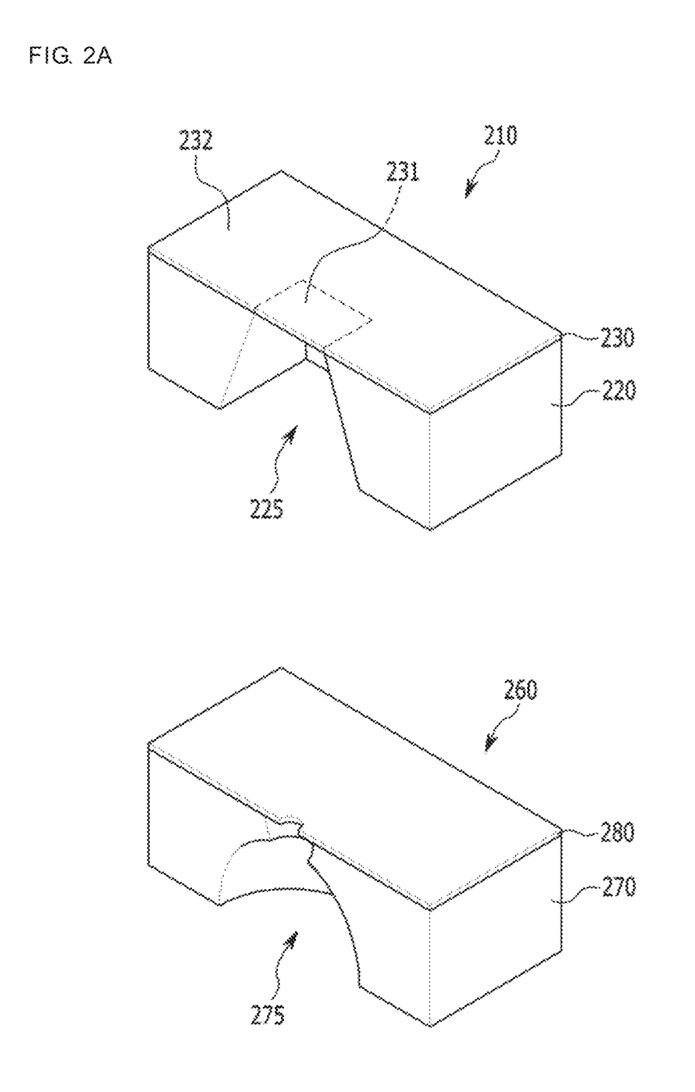
FIGS. 2A to 2D are perspective views illustrating a process of a method of manufacturing a nano membrane structure according to an exemplary embodiment of the present invention.
Figure 2B:
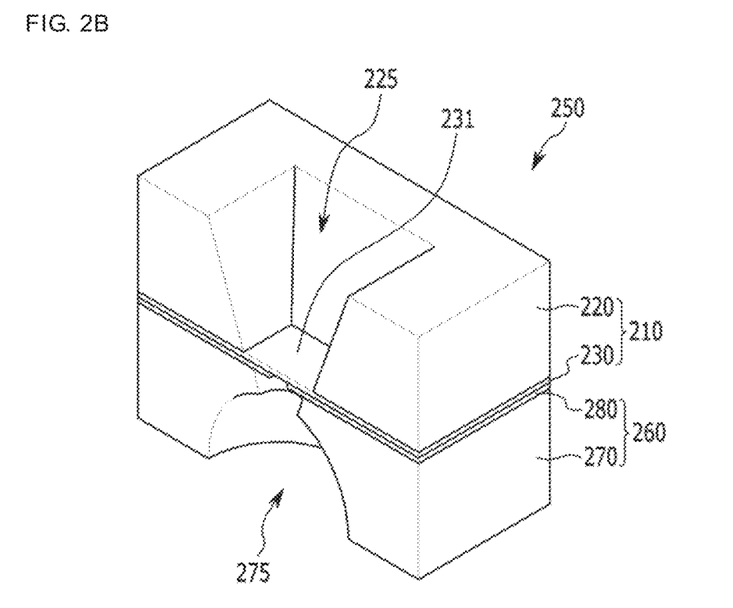
Figure 2C:
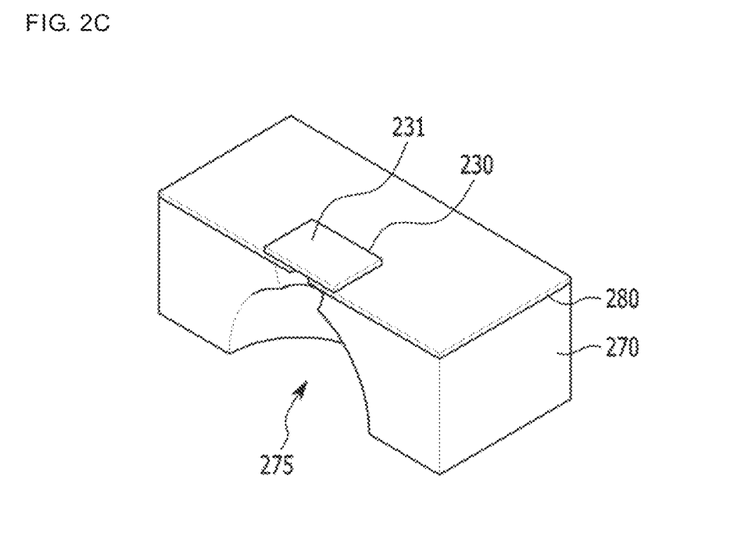
Figure 2D:
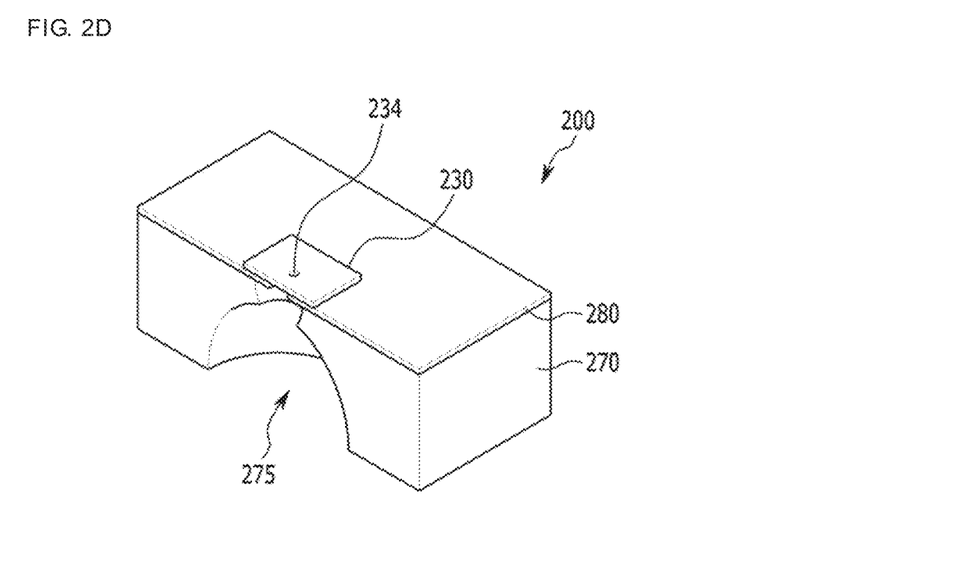
Figure 3A:
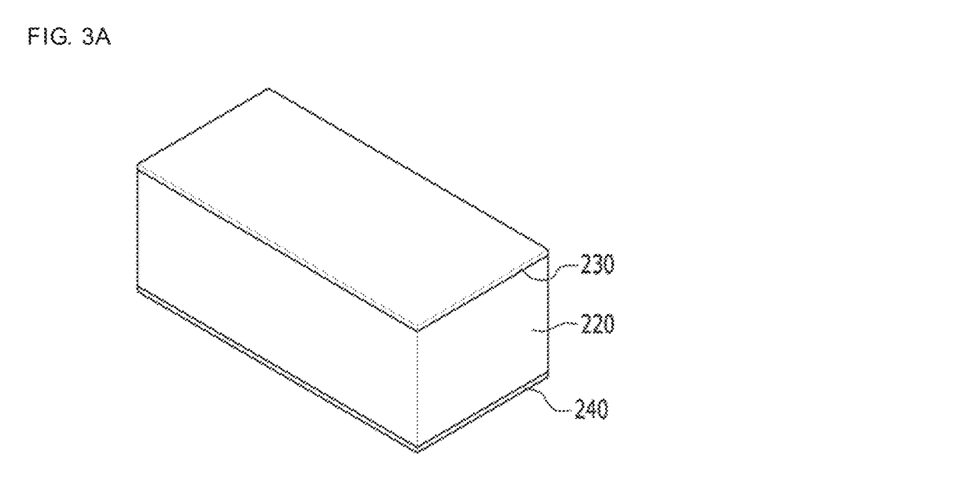
FIGS. 3A to 3C are perspective views illustrating a process of a method of manufacturing a temporary structure.
Figure 3B:
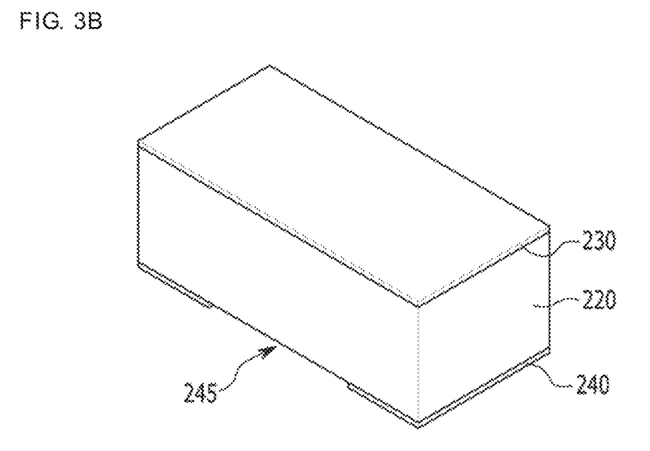
Figure 3C:
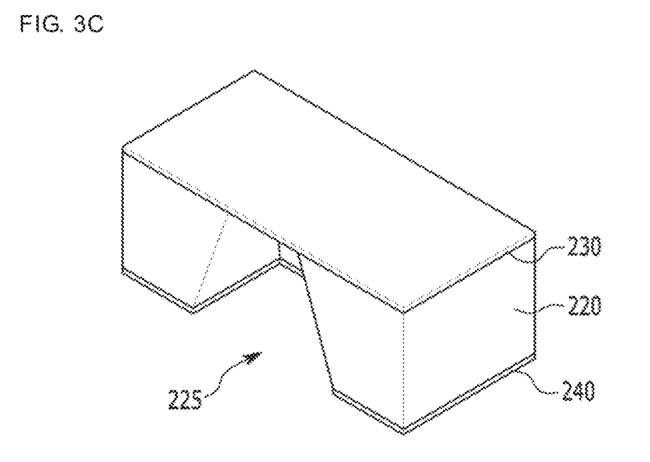

FIGS. 2A to 2D are perspective views illustrating a process of a method of manufacturing a nano membrane structure according to an exemplary embodiment of the present invention, FIGS. 3A to 3C are perspective views illustrating a process of a method of manufacturing a temporary structure, and FIGS. 4A to 4G are perspective views illustrating a process of a method of manufacturing an insulating support member.

Referring to FIGS. 2A to 2D, in a method of manufacturing a nano membrane structure of the present exemplary embodiment, as shown in FIG. 2A, a temporary structure 210 and an insulating support member 260 are prepared.

In the temporary structure 210, a substrate 220 and a nano membrane 230 are provided. The substrate 220 may be a silicon substrate, in a central portion of the substrate 220, a through-hole 225 is formed. The nano membrane 230 includes silicon nitride (SiN) and is disposed to cover the through-hole 225 on the substrate 220. The nano membrane 230 is divided into a central area 231 corresponding to the through-hole 225 of the substrate 220 and a peripheral area 232 formed on the substrate 220. The nano membrane 230 may be silicon nitride formed by a Low Pressure Chemical Vapor Deposition (LPCVD) method, and a thickness of the nano membrane 230 may be tens to hundreds of nanometer. The central area 231 of the nano membrane 230 may have a square shape having a size of several mm. For example, the central area 231 may have a square shape of 2 mm in width and 2 mm in length.

The temporary structure 210 may be produced by a method of FIGS. 3A to 3C.

First, as shown in FIG. 3A, the nano membrane 230 is formed in an upper portion of the substrate 220, and a first mask layer 240 is formed in a lower portion of the substrate 220. The first mask layer 240 is used for forming the through-hole 225 in the substrate 220 and may be made of silicon nitride (SiN). The nano membrane 230 and the first mask layer 240 may be formed by a separate process or one process. For example, when depositing silicon nitride in the substrate 220 by an LPCVD method, in an upper portion and a lower portion of the substrate 220, the nano membrane 230 and the first mask layer 240, respectively, are formed.

Thereafter, as shown in FIG. 3B, by etching a portion of the first mask layer 240, a first etching window 245 is formed. The first etching window 245 may be formed through etching of the first mask layer 240 using a photolithography process and a reactive ion etching process.

Thereafter, as shown in FIG. 3C, by etching the substrate 220 using the first etching window 245, a through-hole 225 is formed in the substrate 220. The through-hole 225 may be formed using a wet etching process. Until a lower surface of the nano membrane 230 is exposed, the substrate 220 is etched. When the substrate 220 is made of silicon, the through-hole 225 may be formed using a wet etching process using KOH. In this case, in view of a silicon etching characteristic of KOH, the through-hole 225 having a cross-section of a square shape may be formed. An upper portion of the substrate 220 is protected by the nano membrane 230.

The insulating support member 260 may be made of an insulating material including at least one of silicon and a compound containing silicon. The insulating support member 260 may include at least one of, for example, silicon (Si), silicon oxide (SiO2), silicon nitride (SiN) and polydimethylsiloxane (PDMS). The insulating support member 260 may be formed with a silicon oxide substrate 270 and an amorphous silicon layer 280 formed on the silicon oxide substrate 270. In a central portion of the insulating support member 260, a micropore 275 that penetrates one side and the other side is formed. The micropore 275 may be formed in a size of several micrometers. Here, a size of the micropore 275 is defined to a size of a hole formed at an upper surface of the insulating support member 260, and as advancing to a lower portion of the insulating support member 260, a size of the micropore 275 may increase. For example, when the insulating support member 260 is formed with the silicon oxide substrate 270 and the amorphous silicon layer 280 formed on the silicon oxide substrate 270, a size of the micropore 275 is defined to a size of a hole formed in the amorphous silicon layer 280, a size thereof may be several micrometers, and a size of a hole formed in the silicon oxide substrate 270 may be tens to hundreds of micrometers.

The insulating support member 260 formed with the silicon oxide substrate 270 and the amorphous silicon layer 280 formed on the silicon oxide substrate 270 may be produced by a method of FIGS. 4A to 4G.

Figure 4A:
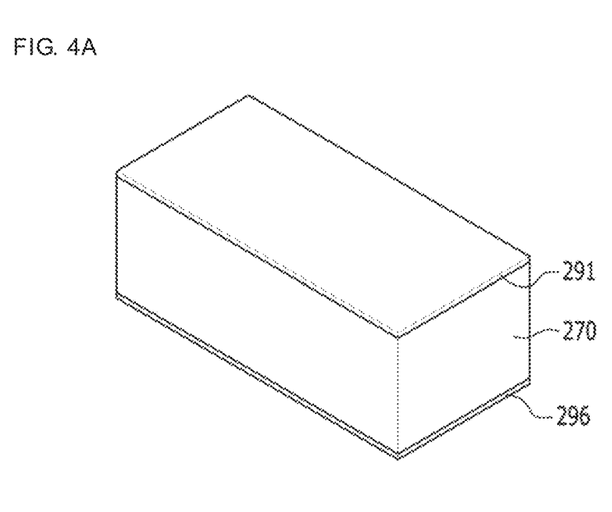
FIGS. 4A to 4G are perspective views illustrating a process of a method of manufacturing an insulating support member.

First, as shown in FIG. 4A, a second mask layer 291 is formed in an upper portion of the silicon oxide substrate 270, and a third mask layer 296 is formed in a lower portion of the silicon oxide substrate 270. The second mask layer 291 and the third mask layer 296 are used for forming the micropore 275 in the insulating support member 260 and may be made of amorphous silicon. The second mask layer 291 and the third mask layer 296 may be formed by a separate process or one process.

Figure 4B:
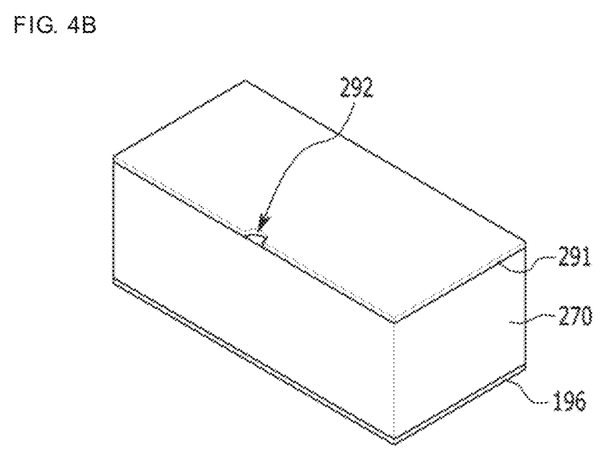

Thereafter, as shown in FIG. 4B, by etching a portion of the second mask layer 291, a second etching window 292 is formed. The second etching window 292 may be formed through etching of the second mask layer 291 using a photolithography process and a reactive ion etching process. The second etching window 292 may be formed in a size of several micrometers.

Figure 4C:
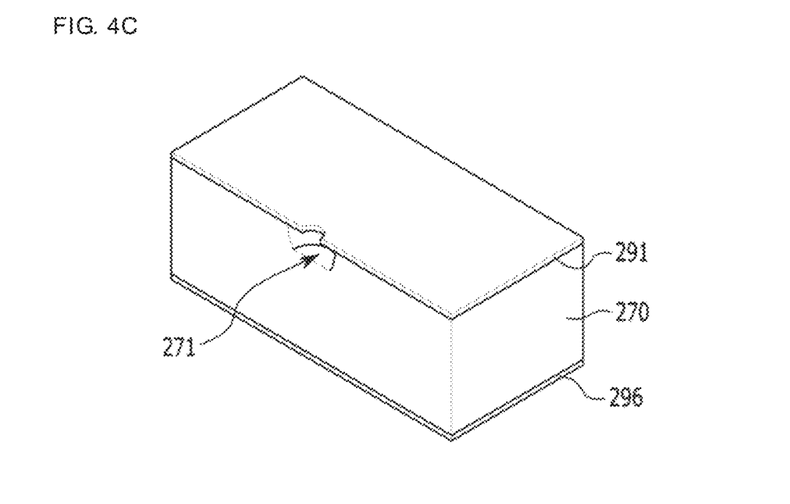

Thereafter, as shown in FIG. 4C, by etching a portion of an upper portion of the silicon oxide substrate 270 using the second etching window 292, in a upper portion of the silicon oxide substrate 270, an upper hole 271 is formed. The upper hole 271 may be formed with a wet etching process. For example, the upper hole 271 may be formed using hydrofluoric acid (HF). When the upper hole 271 is formed with a wet etching process using hydrofluoric acid (HF), undercut occurs due to isotropic etching and thus a size of the upper hole 271 becomes larger than that of the second etching window 292. For example, when the second etching window 292 has a size of several micrometers, the upper hole 271 may be formed in a size of tens of micrometers.

Figure 4D:
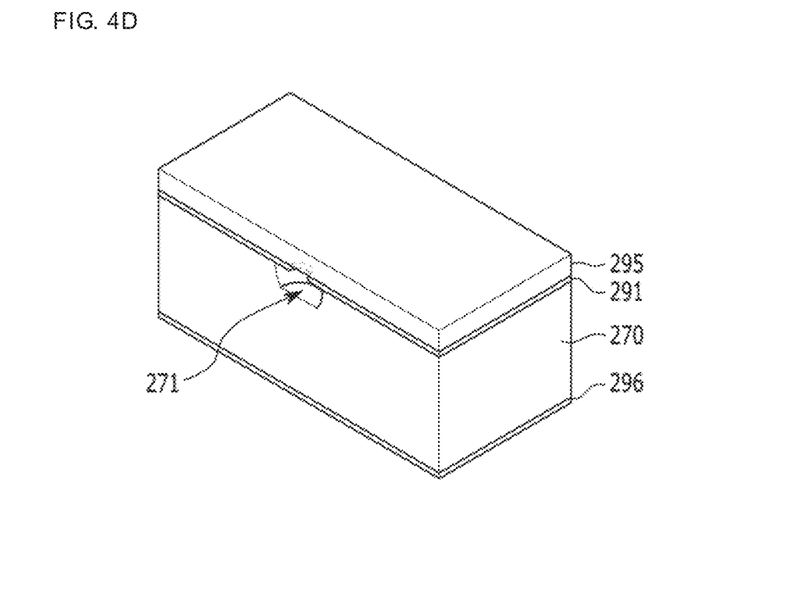

Thereafter, as shown in FIG. 4D, a protective layer 295 is formed on the second mask layer 291. When forming a lower hole 272 to be described later, the protective layer 295 performs a function of protecting the upper hole 271.

Figure 4E:
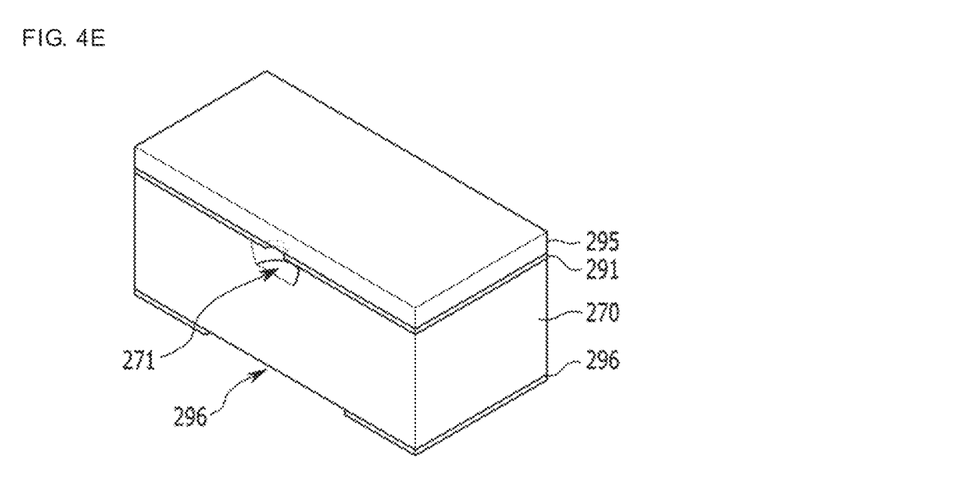

Thereafter, as shown in FIG. 4E, by etching a portion of the third mask layer 296, a third etching window 297 is formed. Forming of the third etching window 297 through etching of the third mask layer 296 may be performed with the same method as that when forming the second etching window 292. The third etching window 297 is formed in a size larger than that of the second etching window 292. The third etching window 297 may be formed in a size of tens to hundreds of micrometers.

Figure 4F:
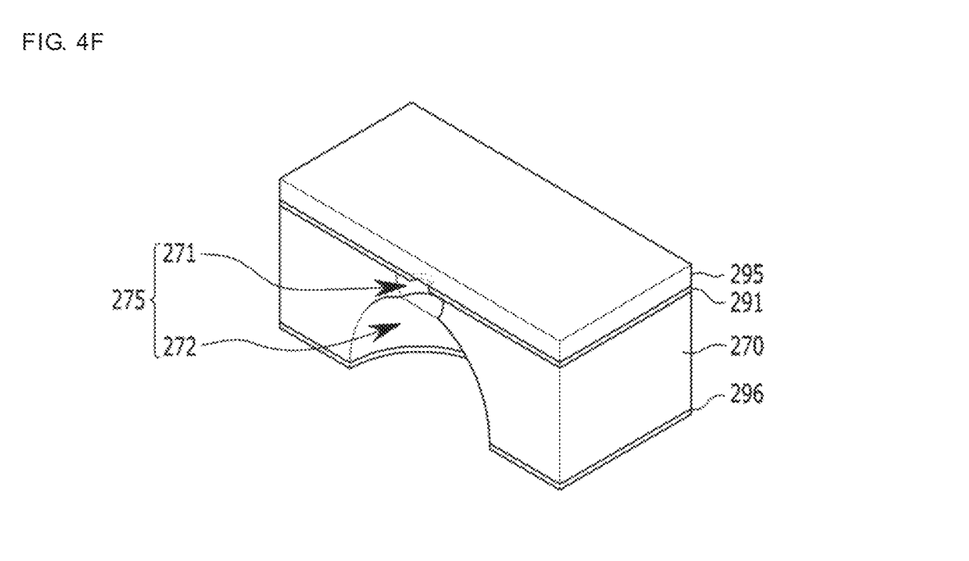

Thereafter, as shown in FIG. 4F, by etching a portion of a lower portion of the silicon oxide substrate 270 using the third etching window 297, in a lower portion of the silicon oxide substrate 270, the lower hole 272 is formed. The lower hole 272 may be formed with the same method as that when forming the upper hole 271. A size of the lower hole 272 may be formed in a size larger than that of the upper hole 271, and a size thereof may be hundreds of micrometers. Etching of the silicon oxide substrate 270 for forming the lower hole 272 is performed until the micropore 275 defined to the upper hole 271 and the lower hole 272 is formed, as the upper hole 271 and the lower hole 272 communicate.

Figure 4G:
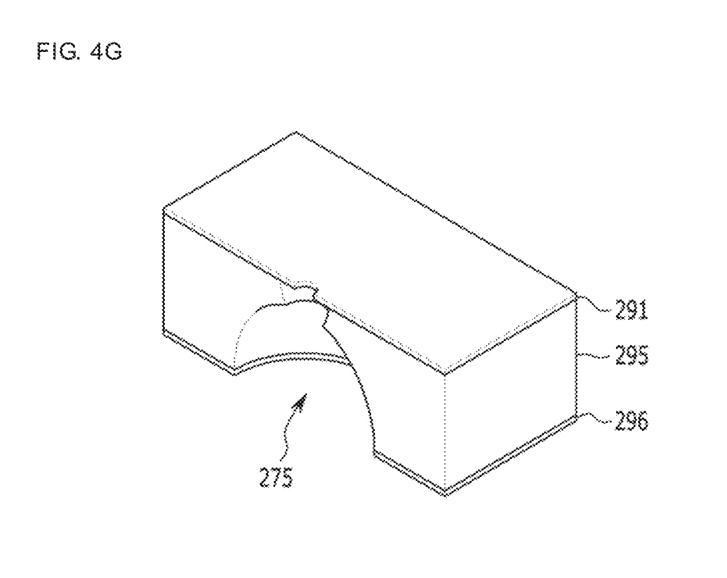

Thereafter, as shown in FIG. 4G, the protective layer 295 is removed. When the protective layer 295 is removed, the second mask layer 291 is exposed in which the second etching window 292 is formed, and the second mask layer 291 corresponds to the amorphous silicon layer 280 of FIG. 2A.

As described above, the temporary structure 210 and the insulating support member 260 may be formed with a method of FIGS. 3A to 4G.

Thereafter, as shown in FIG. 2B, by bonding the nano membrane 230 and the amorphous silicon layer 280 of the temporary structure 210, a complex structure 250 is formed. By performing a hydrophilic surface processing of the nano membrane 230 and the amorphous silicon layer 280 and by bonding the nano membrane 230 and the amorphous silicon layer 280, the complex structure 250 is formed. In this case, in order to enable at least a portion of the central area 231 of the nano membrane 230 to face the micropore 275, the temporary structure 210 and the insulating support member 260 are bonded. In order to perform a hydrophilic surface processing of the nano membrane 230 and the amorphous silicon layer 280 and to bond the nano membrane 230 and the amorphous silicon layer 280, by putting the temporary structure 210 and the insulating support member 260 under water and by contacting the nano membrane 230 and the amorphous silicon layer 280, the nano membrane 230 and the amorphous silicon layer 280 may be bonded.

By exposing the complex structure 250 in air, the complex structure 250 may be dried. The complex structure 250 may be dried in a temperature of 100° C. or less. In this case, while water evaporates, the central area 231 of the nano membrane 230 made of silicon nitride and the amorphous silicon layer 280 are securely adsorbed. Here, the amorphous silicon layer 280 is exemplified, but even when the insulating support member 260 is made of silicon or a compound containing silicon, the central area 231 of the nano membrane 230 containing silicon nitride and the insulating support member 260 are securely adsorbed.

Thereafter, as shown in FIG. 2C, in the complex structure 250, the substrate 220 of the temporary structure 210 is removed. The substrate 220 may be physically removed. The substrate 220 is easily removed even with only a small physical force. When the substrate 220 is physically removed, the peripheral area 232 of the nano membrane 230 may be together removed. However, as described above, because the central area 231 of the nano membrane 230 and the amorphous silicon layer 280 are securely adsorbed, when the substrate 220 is removed, the central area 231 of the nano membrane 230 is not together removed but is remained on the insulating support member 260. Thereby, the nano membrane 230 is formed in which only the central area 231 is remained on the insulating support member 260.

Thereafter, as shown in FIG. 2D, by etching the nano membrane 230 and by forming a nanopore 234 in a central portion of the nano membrane 230, a nano membrane structure 200 having the nanopore 234 may be produced. The nano membrane 230 may be etched using a reactive ion etching process using carbon tetrafluoride (CF4) and may enable to have an etching velocity of about 20 nm per minute when adjusting RF power to about 40 W. Thereby, the nano membrane 230 may have a desired thickness. For example, the nano membrane 230 may be etched in a thickness of about 20 nm. The nanopore 234 is formed in a size smaller than that of the micropore 275 of the insulating support member 260 and is formed to communicate with the micropore 275. The nanopore 234 may be formed using an E-beam.

Figure 5A:
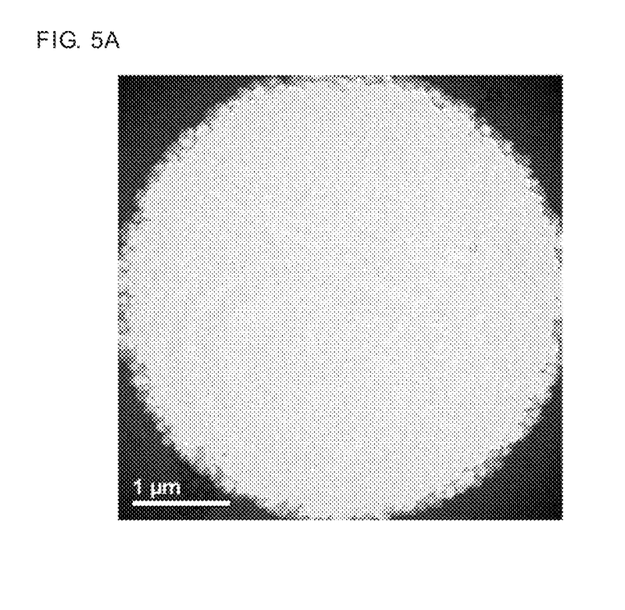
FIG. 5A is a Transmission Electron Microscopy (TEM) picture of a surface of a nano membrane structure produced according to an exemplary embodiment of the present invention.
Figure 5B:
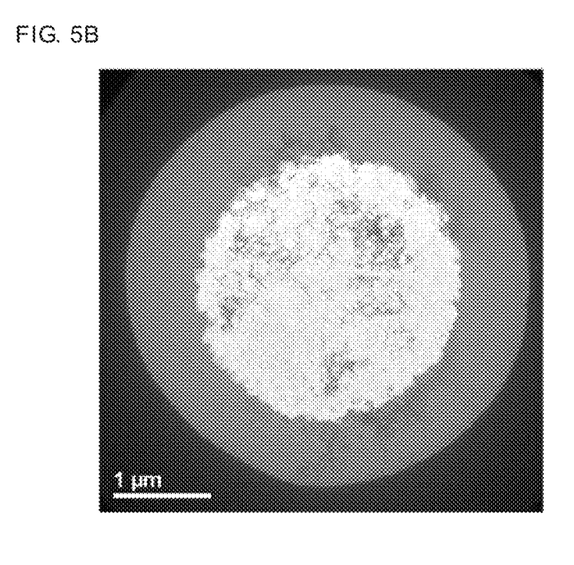
FIG. 5B is a TEM picture of a surface of a nano membrane structure produced using a transfer support layer.

When producing a nano membrane structure 200 having a nanopore with such a method, a transfer support layer such as existing polymethyl methacrylate (PMMA) may not be used and thus a problem does not occur that a transfer support layer exists in a nano membrane structure and this is illustrated in FIG. 5.

FIG. 5A is a Transmission Electron Microscopy (TEM) picture of a surface of a nano membrane structure produced according to an exemplary embodiment of the present invention, and FIG. 5B is a TEM picture of a surface of a nano membrane structure produced using a transfer support layer surface.

As shown in FIGS. 5A and 5B, it can be seen that a nano membrane structure surface produced according to an exemplary embodiment of the present invention is remarkably clean, compared with a nano membrane structure surface produced using a transfer support layer.

Figure 6:
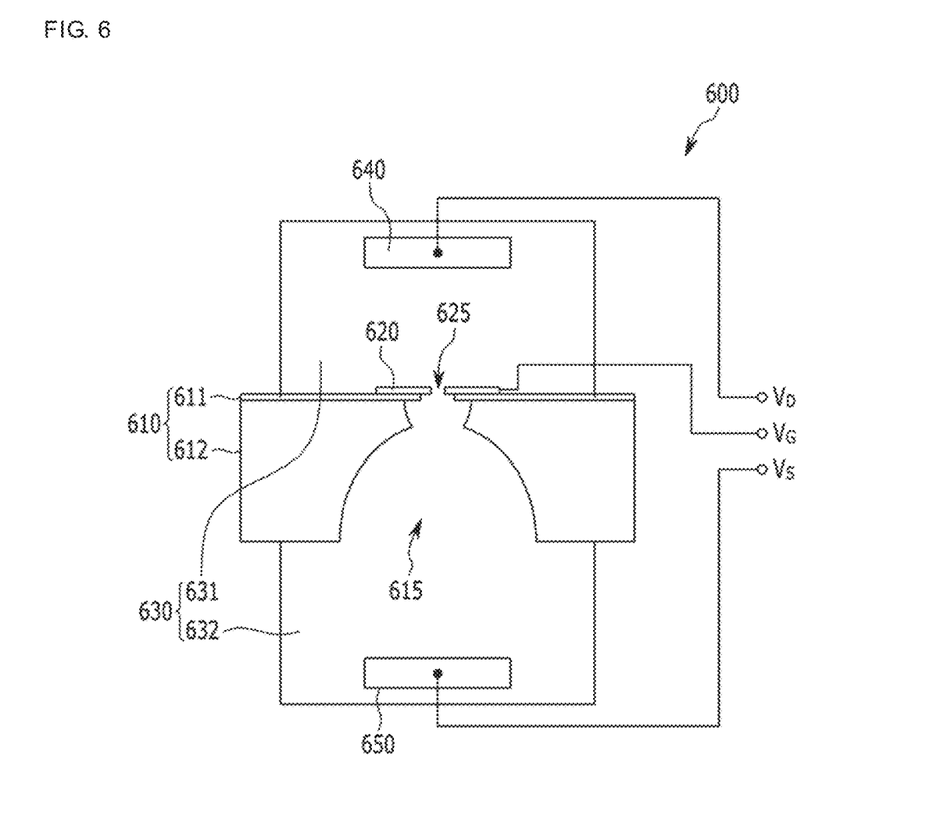
FIG. 6 is a diagram illustrating an ion device using a nanopore structure according to an exemplary embodiment of the present invention.

FIG. 6 is a diagram illustrating an ion device using a nanopore structure according to an exemplary embodiment of the present invention.

Referring to FIG. 6, an ion device 600 using a nanopore structure of the present exemplary embodiment includes a chamber 630, a first electrode 640, a second electrode 650, an insulating support member 610, and a nanopore film 620.

At both sides of the nanopore film 620, a first area 631 and a second area 632 of the chamber 630 are disposed. The first electrode 640 and the second electrode 650 are disposed within the first area 631 and the second area 632, respectively. The nanopore film 620 includes a nanopore 625, and the nanopore 625 may be located, for example, at the center of the nanopore film 620. The first electrode 640 and the second electrode 650 may receive and output an electrical signal from the outside.

The chamber 630 may be divided into the first area 631 and the second area 632 by the nanopore film 620, and the first area 631 and the second area 632 may be formed in a separate chamber. The chamber 630 is used for housing an electrolyte solution, and at the first area 631 and the second area 632 of the chamber 630, the first electrode 640 and the second electrode 650, respectively, are disposed. The chamber 630 may be made of at least one of glass, polydimethylsiloxane (PDMS), and plastic. The chamber 630 may house a solution including an electrolyte, the solution may be prepared in a fluid state and a random conductive solvent may be used. The chamber 630 may further include an injection portion (not shown) that can inject the solution from the outside thereof into the chamber 630 and a discharge portion (not shown) that can discharge the solution from the chamber 630 to the outside thereof. The chamber 630 may have a very little capacity, and a length of any one direction may be a size of several micrometers.

The first electrode 640 may be disposed at the first area 631 of the chamber 630, and the second electrode 650 may be disposed at the second area 632 of the chamber 630. By moving ions within the solution by applying a voltage to the solution within the chamber 630, the first electrode 640 and the second electrode 650 may resultantly occur a current flow. The first electrode 640 and the second electrode 650 may include any one or at least one of aluminum (Al), gold (Au), beryllium (Be), bismuth (Bi), cobalt (Co), hafnium (Hf), indium (In), manganese (Mn), molybdenum (Mo), nickel (Ni), lead (Pb), palladium (Pd), platinum (Pt), rhodium (Rh), rhenium (Re), ruthenium (Ru), tantalum (Ta), tellurium (Te), titanium (Ti), tungsten (W), zinc (Zn), zirconium (Zr), nitride thereof, and silicide thereof. The first electrode 640 and the second electrode 650 may each be a single layer or a complex layer. For example, the first electrode 640 and the second electrode 650 may be a complex layer of silver (Ag) or silver chloride (AgCl). The first electrode 640 and the second electrode 650 may include the same material or a different material. Further, the first electrode 640 and the second electrode 650 may be disposed adjacent to the nanopore film 620.

The insulating support member 610 may be made of an insulating material including at least one of silicon and a compound containing silicon. The insulating support member 610 may include at least one of, for example, silicon (Si), silicon oxide (SiO2), silicon nitride (SiN), and polydimethylsiloxane (PDMS). The insulating support member 610 may be formed with a silicon oxide substrate 611 and an amorphous silicon layer 612 formed on the silicon oxide substrate 611. In a central portion of the insulating support member 610, a micropore 615 that penetrates one side and the other side is formed. The micropore 615 may be formed in a size of several micrometers. The micropore 615 may be formed using an etching process. Here, a size of the micropore 615 is defined to a size of a hole formed at an upper surface of the insulating support member 610, i.e., the nanopore film 620 and a corresponding surface, and as advancing to a lower portion of the insulating support member 610, a size of the micropore 615 may increase. For example, when the insulating support member 610 is formed with the silicon oxide substrate 611 and the amorphous silicon layer 612 formed on the silicon oxide substrate 611, a size of the micropore 615 is defined to a size of a hole formed in the amorphous silicon layer 612, a size thereof may be several micrometers, and a size of a hole formed in the silicon oxide substrate 611 may be tens to hundreds of micrometers.

The nanopore film 620 may include silicon nitride (SiN). The nanopore film 620 includes a nanopore 625 formed in a central portion, and the nanopore 625 penetrates the nanopore film 620. The nanopore 625 is formed to communicate with the micropore 615 of the insulating support member 610, and the nanopore 625 is formed in a size smaller than that of the micropore 615. The nanopore 625 may be formed in a nano size and may be formed using an E-beam. A thickness of the nanopore film 620 may be from several nanometers to tens of nanometers. The nanopore film 620 may be silicon nitride formed by a Low Pressure Chemical Vapor Deposition (LPCVD) method. Because silicon nitride formed by an LPCVD method has a higher density than that of silicon nitride formed by a Plasma Enhanced Chemical Vapor Deposition (PECVD) method, silicon nitride may be used for a long time period without a size change of the nanopore 625.

The insulating support member 610 and the nanopore film 620 are attached by a hydrophilic surface processing. The insulating support member 610 and the nanopore film 620 may each be formed by supplying moisture to a surface thereof, bonding, and drying. For this reason, the insulating support member 610 and the nanopore film 620 may be attached under water.

The nanopore film 620, the first electrode 640, and the second electrode 650 are connected to an external device (not shown) and each of the nanopore film 620, the first electrode 640, and the second electrode 650 may receive an electrical signal, for example, a voltage and output an electrical signal, for example, a current. A voltage applied to the nanopore film 620 may be referred to as a gate voltage VG, a voltage applied to the first electrode 640 may be referred to as a source voltage VS, and a voltage applied to the second electrode 650 may be referred to as a drain voltage VD. The external device (not shown) may be electrically connected to the nanopore film 620, the first electrode 640, and the second electrode 650 through a conductive member, for example, a conductive wire, and particularly, a portion connected to the nanopore film 620 may be connected by a probe (not shown). Alternatively, the conductive member may be a nano wire, and by forming a constant pattern with a metal and using ion implantation or sputtering, the nano wire may be deposited into a conductive wire.

By a gate voltage VG, a source voltage VS, and a drain voltage VD applied by the external device (not shown), the ion device 600 may operate as an ionic field effect transistor (IFET). The IFET has a similar principle to that of a common semiconductor field effect transistor except that carriers moving a channel are electrolyte ions instead of an electron or a hole. Therefore, an ion current flows by an ion movement instead of an electron movement, and the nanopore 625 operates as a channel for an ion movement. When an electrolyte solution is housed within the chamber 630, ionized positive ions and negative ions may move in any one direction by a source voltage VS and a drain voltage VD applied to the chamber 630, an on-state and an off-state of the transistor may be controlled by a gate voltage VG applied to the nanopore film 620. When a biomaterial such as DNA and RNA exists within the chamber 630, the biomaterial represents a presents a predetermined electric charge and may move, as in ions.

Figure 7:
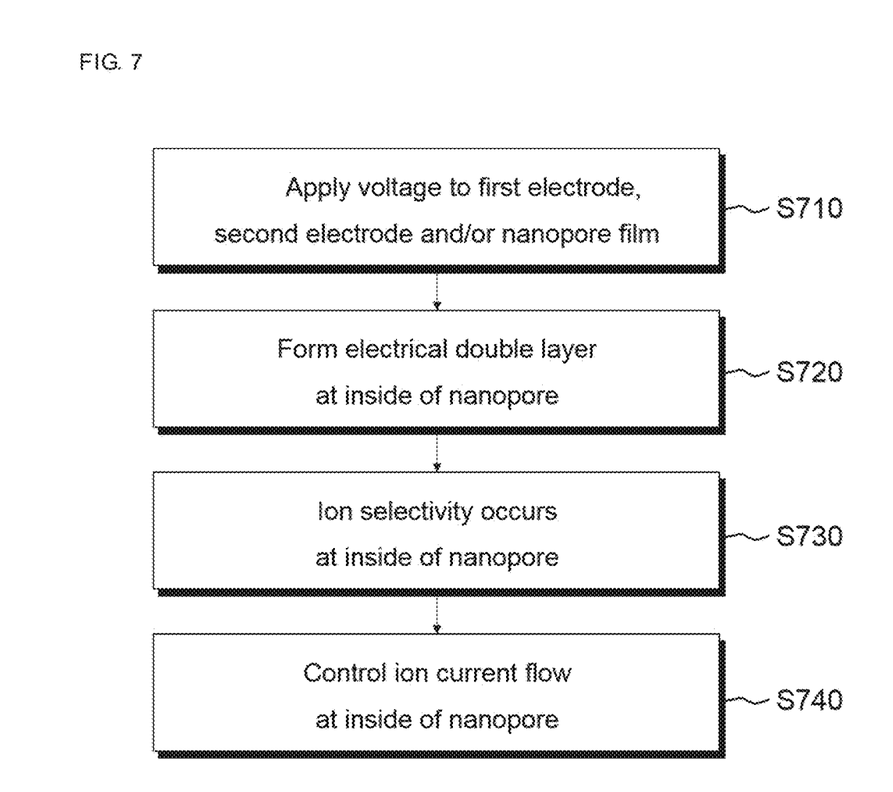
FIG. 7 is a flowchart illustrating an operation principle of an ion device using a nanopore structure according to an exemplary embodiment of the present invention.

FIG. 7 is a flowchart illustrating an operation principle of an ion device using a nanopore structure according to an exemplary embodiment of the present invention.

Referring to FIGS. 6 and 7, an external device (not shown) applies a predetermined voltage to the first electrode 640, the second electrode 650 and/or the nanopore film 620 (S710). For example, a positive gate voltage VG and drain voltage VD and a negative source voltage VS may be applied. At step S710, only the source voltage VS and the drain voltage VD instead of a separate voltage may be applied to the gate voltage VG.

When a voltage is applied, at the inside of the nanopore 625, an electrical double layer is formed (S720). When the gate voltage VG is applied, a surface of a side surface of the nanopore 625 represents a specific electric charge, and an electrical double layer formed with ions having an opposite electric charge is formed. In this way, a phenomenon that covers a surface electric charge may be analyzed by a Debye length, and a Debye length is inversely proportional to the square root of the concentration of an electrolyte within a solution.

When the electrical double layer is formed, the inside of the nanopore 625 has ion selectivity (S730). When the nanopore 625 has a small size, at the inside of the nanopore 625, an electrical double layer is overlapped and thus the inside of the nanopore 625 is filled with opposite ions, and the nanopore 625 may have ion selectivity. In this case, a kind and quantity of ions existing within the nanopore 625 are not changed according to the concentration of a solution and thus in order to enable saturation of ion conductance to occur, a concentration segment occurs, and such ion selectivity becomes a base operating as an ion transistor.

When the nanopore 625 has ion selectivity, as described above, an ion current flow within the nanopore 625 may be controlled (S740). Ions of a specific electric charge may flow according to a magnitude of the applied gate voltage VG, source voltage VS, and drain voltage VD, and a quantity of an ion current may be controlled. For example, when a positive voltage is applied to the gate voltage VG, a channel of a negative ion may be formed within the nanopore 625, and when a negative voltage is applied to the gate voltage VG, a channel of a positive ion may be formed.

In an exemplary embodiment, the ion device 600 using a nanopore may be used as a DNA analysis apparatus for analyzing a biomolecule. In this case, at the inside of the chamber 630, a solution including a biomolecule such as DNA is housed. An analysis target is not limited to DNA but may be DNA, RNA, peptide, or protein. The solution may use an electrolyte solution such as hydrochloric acid (HCl), sodium chloride (NaCl), or potassium chloride (KCl).

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

| [Description of symbols] | |
|---|---|
| 100: nanopore structure | 110, 260, 610: insulating support member |
| 115, 225, 615: micropore | 120, 620: nanopore film |
| 125, 234, 625: nanopore | 230: nano membrane |
| 600: ion device | 630: chamber |
| 640: first electrode | 650: second electrode |

What is claimed is:

1. A method of manufacturing a nano membrane structure, the method comprising:
   preparing a temporary structure having
      a substrate in which a through-hole is formed in a central portion, and
      a nano membrane comprising silicon nitride (SiN), that covers the through-hole on the substrate, and comprising
         a central area formed on the through-hole, and
         a peripheral area formed on the substrate;
   preparing an insulating support member comprising at least one of silicon and a compound containing silicon, and in which a micropore is formed in a central portion;
   forming a complex structure by performing a hydrophilic surface processing of a surface of the nano membrane and one surface of the insulating support member and by bonding the temporary structure and the insulating support member so that at least a portion of the central area of the nano membrane and the micropore face; and
   removing the substrate from the complex structure.

2. The method of claim 1, wherein the forming the complex structure is performed under water.

3. The method of claim 2, further comprising:
   drying the complex structure between forming the complex structure and the removing the substrate.

4. The method of claim 3, wherein removing the substrate comprises physically removing the substrate.

5. The method of claim 3, wherein removing the substrate comprises removing the peripheral area of the nano membrane when removing the substrate.

6. The method of claim 3, wherein the insulating support member comprises a silicon oxide substrate and an amorphous silicon layer formed on the silicon oxide substrate, and
   forming the complex structure comprises forming the complex structure by bonding the nano membrane and the amorphous silicon layer.

7. The method of claim 3, further comprising:
   forming a nanopore communicating with the micropore and having a size smaller than that of the micropore in the central area of the nano membrane.

8. The method of claim 7, further comprising:
   etching the nano membrane between drying the complex structure and forming the nanopore.

9. The method of claim 7, wherein forming the nanopore comprises forming a hole of a nano size using an E-beam.

10. The method of claim 7, wherein the substrate is a silicon substrate, and the central area of the nano membrane has a square shape having a size of several mm and has a size larger than that of the micropore.

* * * * *